US00PP17552P3

(12) United States Plant Patent
Adam

(10) Patent No.: US PP17,552 P3
(45) Date of Patent: Apr. 3, 2007

(54) CLIMBER ROSE PLANT NAMED 'ADABARING'

(50) Latin Name: *Rosa hybrida*
Varietal Denomination: ADABARING

(75) Inventor: Michel Adam, Liffre (FR)

(73) Assignee: Lux Riviera S.r.l., Bevera di Ventimiglia (IT)

( * ) Notice: Subject to any disclaimer, the term of this patent is extended or adjusted under 35 U.S.C. 154(b) by 0 days.

(21) Appl. No.: 11/090,921

(22) Filed: Mar. 24, 2005

(65) Prior Publication Data

US 2005/0223444 P1 Oct. 6, 2005

(30) Foreign Application Priority Data

Mar. 31, 2004 (EM) ..... 2004/630

(51) Int. Cl.
*A01H 5/00* (2006.01)

(52) U.S. Cl. ..... Plt./115
(58) Field of Classification Search ..... Plt./115, Plt./130, 139, 140
See application file for complete search history.

(56) References Cited

PUBLICATIONS

Haring, ed., 1986, Modern Roses 9, The American Rose Society, Schreveport, Louisiana, p. 199.*

* cited by examiner

*Primary Examiner*—Howard J. Locker
(74) *Attorney, Agent, or Firm*—Klarquist Sparkman, LLP

(57) ABSTRACT

Climber rose plant having vigor; more numerous leaves than the 'DELSIRE' cultivar; dark red color; better climbing-up capability than the 'DELSIRE' cultivar; disease resistance; and strong fragrance.

1 Drawing Sheet

Figure 1:
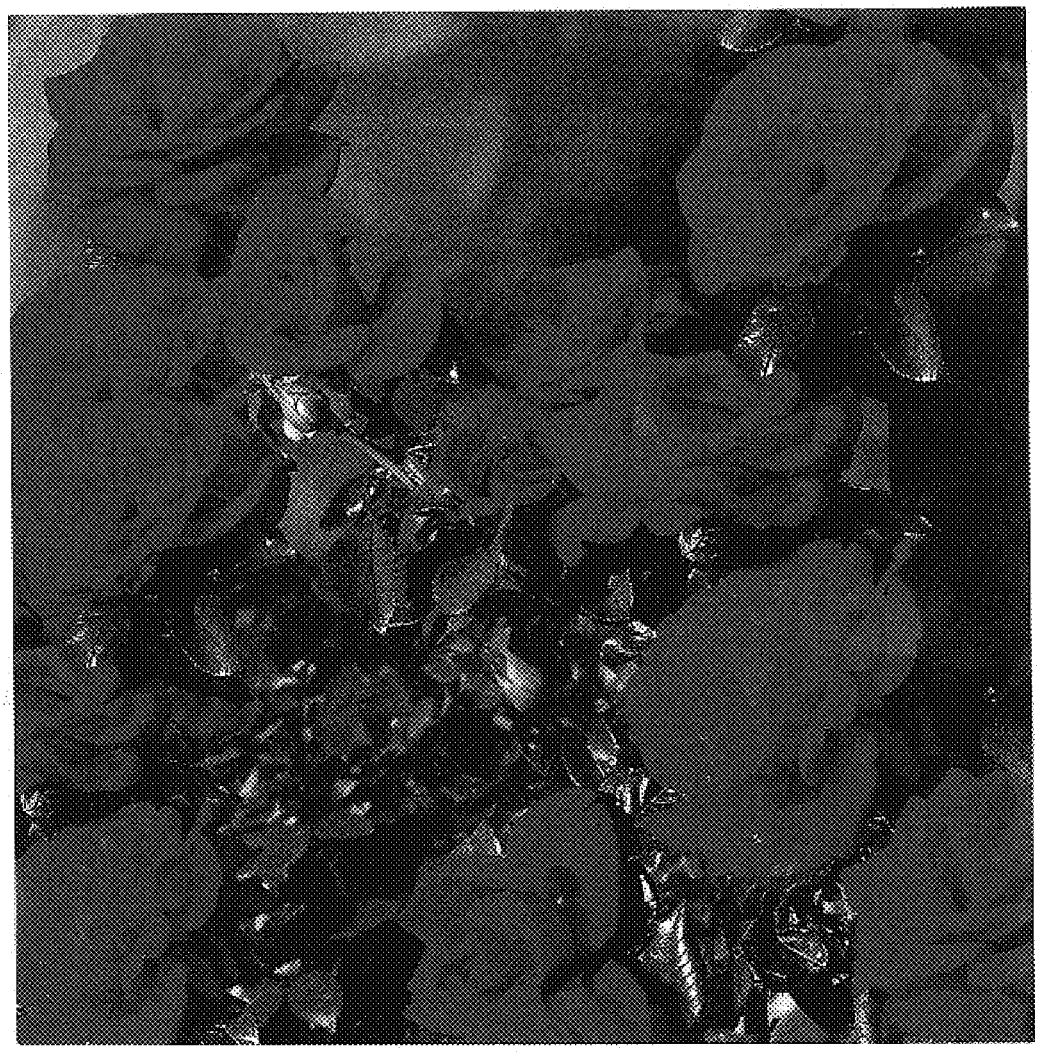

Genus and species: *Rosa hybrida.*
Variety denomination: 'ADABARING'.

ORIGIN OF THE INVENTION

The present invention relates to a new and distinct variety of a climber rose plant named 'ADABARING' which was originated by me by crossing the variety 'DELSIRE' (unpatented), with the variety 'MEITULIMON' (unpatented).

BACKGROUND OF THE INVENTION

The primary objective of this breeding was to produce a new rose variety having a large double red climbing rose, strong foliage with more vigor and energy, a better climbing-up activity and a dark red color.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. More vigor in comparison to the 'DELSIRE' cultivar.
2. More leaves in comparison to the 'DELSIRE' cultivar.
3. Dark red flowers.
4. Better climbing-up capability in comparison to the 'DELSIRE' cultivar.
5. Disease resistance to black spot and *Sphaeroteca pannosa.*
6. Extremely fragrant in comparison to the 'DELSIRE' cultivar.

Asexual reproduction of this new variety by grafting onto *Rosa multiflora* (unpatented) rootstock, as performed at Liffre, France, shows that the foregoing and all other characteristics and distinctions come true to form and are established and transmitted through succeeding propagations.

Comparison with Parents

The female parent 'DELSIRE' is less fragrant, has bigger leaves, is less vigorous, and in comparison to 'ADABARING'. 'DELSIRE' has deep crimson red flowers. The male parent 'MEITULIMON' is less vigorous and has mauve-pink flowers in comparison to 'ADABARING'.

Comparison with Similar Variety

With reference to the above comparison with the parent plants, 'DELSIRE' is believed to be the most similar cultivar to the new 'ADABARING' plant.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated. It should be noted that color is difficult to determine precisely and can vary with growing conditions.

Parentage:
*Seed parent.*—'DELSIRE'.
*Pollen parent.*—'MEITULIMON'.

FLOWER

Observations were made over an eight year period. Then following observations are of eight year old plants grown on multiflora rootstock in a garden environment at Liffre, France.

Blooming habit: From May until frost.

Bud:

*Size.*—About 1.6 cm in diameter when the petals start to unfurl.

*Form.*—The bud form is pointed ovoid.

*Color.*—When sepals first divide, bud color is rouge cardinal (RHS 53A). When half blown, the upper sides of the petals are strong red (RHS 53A), and the lower sides of the petals are strong red (RHS 53A).

*Sepals.*—Color: Upper surface: Yellow-green (RHS 140B). Lower surface: Yellow-Green (RHS 140A). Length: 3–4 cm. Width: 1.3–1.5 cm. Shape: Elongated. Surface texture: Smooth. There are three normally appendaged sepals. There are two unappendaged sepals with smooth edges.

*Receptacle.*—Color: Green (RHS 141A). Shape: Funnel. Size: Medium, about 1.5 cm long×1.5 cm wide. Surface: Smooth.

*Peduncle.*—Length: Long, averaging about 5–8 cm long. Surface: Rough. Color: Green (RHS 142A). Strength: Stiff, erect.

Bloom:

*Size.*—Large. Average open diameter is about 13 cm to 16 cm.

*Borne.*—Singly and several together in clusters of 3–5 blooms having rounded shape.

*Stems.*—Strength: Normal. Average length is about 30–60 cm with a diameter of 3–5 mm.

*Form.*—When first open: High centered. Permanence: Flattens toward the end of the bloom.

*Petalage.*—Number of petals under normal conditions: 23–30.

*Color.*—The upper sides of the petals are strong red (RHS 53A). The reverse sides of the petals are less strong red (RHS 53A). The base of the petal is a strong red (RHS 53B) with yellow nuances (RHS 150C). The major color on the upper side is strong red (RHS 53A).

*Variegations.*—None observed.

*Discoloration.*—The general tonality at the end of the first day is red (from Red Group RHS 53A to Red Group 53B). At the end of the third day the general tonality is reddish-purple- (from RHS 59A to RHS 60A). Further aging: No change.

*Fragrance.*—Strong, spicy.

Petals:

*Texture.*—Thick.

*Shape.*—Oval.

*Surface.*—Smooth.

*Margin.*—Smooth.

*Apex shape.*—Rounded.

*Base shape.*—Acute.

*Form.*—Edges slightly quilled.

*Arrangement.*—Informal.

*Petaloids.*—Number: 5 to 10. Color: Red (RHS 59A).

*Persistence.*—Petals hang on and dry.

*Lastingness.*—On the plant: Long. Has not been systematically observed so as to be expressed relative to number of days. As a cut flower: Not tested or systematically observed.

Reproductive parts:

*Stamens.*—Number: Many. Length: Normal. Anthers: Length: Normal. Color: Yellow (RHS 22B) sometimes with a little red (RHS 42A). Arrangement: Regular around styles. Filaments: Color: Red (RHS 42A). Length: 1.4 cm. Pollen: Color: Yellow (RHS 22C).

*Pistils.*—Number: 60. Length: 0.5 to 0.8 cm. Styles: Color: Length: Normal. Stigmas: Color: Orange-Red (RHS 35C). Length: Normal.

*Hips.*—Color: Orange (RHS 24A). Size: 2.3 cm.

PLANT

*Form.*—Climber.

*Growth.*—Very vigorous.

*Age at maturity.*—3 years.

*Mature plant.*—Height: Three to four meters. Width: Often 150 cm to 180 cm.

*Rootstock.*—Multiflora.

Foliage: Number of leaflets on normal mid-stem leaves: 5.

*Size.*—Medium. About 5 cm long and 7/10 wide.

*Quantity.*—Abundant.

*Color.*—New foliage: Upper side: Greyed-Purple (RHS 187B–187C). Lower side: Greyed-Purple (RHS 187B). Old foliage: Upper side: Brilliant Green (RHS 139A). Lower side: Green (RHS 139B).

Leaflets:

*Size.*—About 6 cm long×3 cm wide.

*Shape.*—Pointed oval.

*Base shape.*—Acute.

*Texture/appearance.*—Leathery. Glazed or shiny surface.

*Edge.*—Serrated.

*Serrations.*—Single, small.

*Petiole.*—Color: Pale green (RHS 141A).

*Petiole rachis.*—Color: Base, clear green (RHS 141D). Underside: With prickles.

*Auricles.*—2.

*Stipules.*—Length: 1 cm, smooth.

*Disease resistance.*—Resistant to mildew, resistant to rust and resistant to blackspot under normal growing conditions.

*Pest resistance.*—Good resistance to pests.

Wood:

*New wood.*—Color: Green (RHS 136B). Bark: Smooth.

*Old wood.*—Color: Green (RHS 140A). Bark: Rough.

Prickles:

*Quantity.*—On main canes from base: Few 10–15 per 6 cm of cane length. On laterals from main canes: Few.

*Form.*—Hooked downward.

*Length.*—0.3 to 0.5 cm.

*Color when young.*—Greyed-red (RHS 181A).

*Color when mature.*—Greyed-red (RHS 181B).

Small prickles:

*Quantity.*—On main stalks: Few. On laterals: Few.

*Color.*—When young: Greyed-red (RHS 181A). When mature: Greyed-red (RHS 181B).

Winter hardiness: Not tested.

I claim:

1. A new and distinct variety of rose plant of the climber class, substantially as herein shown and described, characterized particularly by its vigor; more numerous leaves than the 'DELSIRE' cultivar; dark red color; better climbing-up capability than the 'DELSIRE' cultivar; disease resistance; and strong fragrance.

* * * * *

UNITED STATES PATENT AND TRADEMARK OFFICE

CERTIFICATE OF CORRECTION

PATENT NO. : PP 17,552 P3
APPLICATION NO. : 11/090921
DATED : April 3, 2007
INVENTOR(S) : Michel Adam It is certified that error appears in the above-identified patent and that said Letters Patent is hereby corrected as shown below:

In Column 2, line 28, “IIorticulture” should read -- Horticultural --

In Column 3, line 39, “23 30” should read -- 23-30 --

In Column 3, line 41, “(RIIS 53A)” should read -- (RHS 53A) --

In Column 3, line 50, “reddish-purple-” should read -- reddish-purplish --

Signed and Sealed this

Eighteenth Day of December, 2007

JON W. DUDAS
*Director of the United States Patent and Trademark Office*